(12) United States Patent
Klein Hubert et al.

(10) Patent No.: US 11,034,031 B2
(45) Date of Patent: Jun. 15, 2021

(54) TOOL COUPLING

(71) Applicants: FUNDACIÓN TECNALIA RESEARCH & INNOVATION, Vizcaya (ES); UNIVERSIDAD DE CÓRDOBA, Córdoba (ES); SERVICIO ANDALUZ DE SALUD, Seville (ES); UNIVERSIDAD DE MÁLAGA, Málaga (ES)

(72) Inventors: Julius Klein Hubert, Vizcaya (ES); Asier Fernández Iribar, Vizcaya (ES); Rafael Medina Carnicer, Cordova (ES); Rafael Muñoz Salinas, Cordova (ES); Enrique Bauzano Núñez, Málaga (ES); Mª Carmen López Casado, Málaga (ES); Víctor Fernando Muñoz Martínez, Málaga (ES); María José Requena Tapia, Cordova (ES); José Eduardo Arjona Berral, Cordova (ES); Rosa María Paredes Esteban, Cordova (ES); Ángel Salvatierra Velázquez, Cordova (ES); Ignacio Muñoz Carvajal, Cordova (ES); Javier Briceño Delgado, Cordova (ES)

(73) Assignees: FUNDACIÓN TECNALIA RESEARCH & INNOVATION, Vizcaya (ES); UNIVERISAD DE CÓRDOBA, Cordova (ES); SERVICIO ANDALUZ DE SALUD, Seville (ES); UNIVERISAD DE MÁLAGA, Málaga (ES)

( * ) Notice: Subject to any disclaimer, the term of this patent is extended or adjusted under 35 U.S.C. 154(b) by 0 days.

(21) Appl. No.: 16/312,860

(22) PCT Filed: Jun. 23, 2017

(86) PCT No.: PCT/EP2017/065597
§ 371 (c)(1),
(2) Date: Dec. 21, 2018

(87) PCT Pub. No.: WO2017/220805
PCT Pub. Date: Dec. 28, 2017

(65) Prior Publication Data
US 2019/0217483 A1    Jul. 18, 2019

(30) Foreign Application Priority Data
Jun. 23, 2016   (EP) ..................................... 16382294

(51) Int. Cl.
*B25J 15/04*    (2006.01)
*B23B 31/107*   (2006.01)
(Continued)

(52) U.S. Cl.
CPC .......... *B25J 15/0408* (2013.01); *B25J 15/04* (2013.01); *A61B 34/30* (2016.02);
(Continued)

(58) Field of Classification Search
CPC ............... B25J 15/0408; B25J 1515/04; A61B 2018/00172; A61B 2090/064; A61B 34/30; A61B 2017/00477
See application file for complete search history.

(56) References Cited

U.S. PATENT DOCUMENTS 4,227,853 A   10/1980   Woodford et al.
5,762,458 A    6/1998   Wang et al.
(Continued)

OTHER PUBLICATIONS

International Search Report dated Oct. 18, 2017 re: Application No. PCT/EP2017/065597, pp. 1-7, citing: U.S. Pat. No. 4,227,853 A, U.S. Pat. No. 5,762,458 A, U.S. Pat. No. 6,062,575 A and US 2013/340238 A1.
(Continued)

*Primary Examiner* — Eric A. Gates
*Assistant Examiner* — Paul M Janeski
(74) *Attorney, Agent, or Firm* — Cantor Colburn LLP

(57) ABSTRACT

A tool coupling includes a first tool part and a second tool part, the second tool part being movable in relation to the
(Continued)

first tool part. The tool coupling further includes a first base part for detachably retaining the first tool part and a second base part movable in relation to the first base part for detachably retaining the second tool part. The first base part has a pusher movable in relation to the first base part for detaching the first tool part and the second base part has a cap movable in relation to the second base part for detaching the second tool part.

8 Claims, 7 Drawing Sheets

(51) Int. Cl.
*A61B 17/00* (2006.01)
*A61B 18/00* (2006.01)
*A61B 90/00* (2016.01)
*A61B 34/30* (2016.01)

(52) U.S. Cl.
CPC .............. *A61B 2017/00477* (2013.01); *A61B 2018/00172* (2013.01); *A61B 2090/064* (2016.02); *B23B 31/107* (2013.01)

(56) References Cited

U.S. PATENT DOCUMENTS

| | | | |
|---|---|---|---|
| 6,062,575 | A | 5/2000 | Mickel et al. |
| 9,676,096 | B2 * | 6/2017 | Roberts ................ B25J 9/16 |
| 2013/0340238 | A1 | 12/2013 | Shores et al. |

OTHER PUBLICATIONS

Written Opinion dated Oct. 18, 2017 re: Application No. PCT/EP2017/065597, pp. 1-7, citing: U.S. Pat. No. 4,227,853 A, U.S. Pat. No. 5,762,458 A and U.S. Pat. No. 6,062,575 A.

* cited by examiner

TOOL COUPLING

TECHNICAL FIELD

The present disclosure relates to a tool coupling and especially to a mechanical coupling for coupling tools to a distal end of a robot arm, machine tool or similar.

BACKGROUND

Machine tools, surgical robots arms, and other devices need to have the specific tools disposed at their ends changed. Those tools might be clamps, soldering instruments, cutters, etc. and quite often have moving parts. In order to operate any moving parts, an element as, for instance, a Bowden cable or similar element is usually installed. Another option is to install a torque transmitter between the machine (driving device) and the tool (driven device), through the coupling.

An example of those tools would be the surgical tools sold under the brand CLICKline® Instruments by Karl Storz (Germany).

When the robot or machine tool has to do delicate works such as surgical operations or certain industrial processes, it has to be carefully controlled so that it operates gently and precisely. Furthermore, this kind of works usually require using different tools, which means plenty of time wasted in coupling and uncoupling operations. Therefore, there is a need for coupling mechanisms between the tool and the tool holder that provide a rigid and precise coupling and an easy quick coupling and uncoupling of different tools while allowing some kind of movement transmission to a moving subset of the tool.

SUMMARY

The present disclosure seeks to provide a tool coupling device which facilitates a mechanical coupling between a tool and a base. The tool comprises a first part and a second part and the second tool part is movable in relation to the first tool part. The first tool part can comprise an axial hole where the second part moves back and forth. The second tool part can be a reciprocating rod or a cable or a torque transmitter. The free end of the tool can be inserted in a hole of the base which is equipped with retainers for the tool.

The base can be a tool holder in a machine-tool or industrial robot. Preferably the base is a surgical robot and the tool is a surgical tool.

According to the disclosure, the base comprises a first base part for detachably retaining the first tool part of the tool to be coupled and a second base part for detachably retaining the second tool part of the tool to be coupled. The second base part is movable in relation to the first base part. The first base part further comprises a pusher for detaching the first tool part, when the tool is coupled to the tool coupling, and the second base part comprises a cap for detaching the second tool part, when the tool is coupled to the tool coupling.

In one embodiment the first base part comprises at least one first lock element and a first sloped guide, the first lock element being housed in the first sloped guide and movable from a first locking position to a second non-locking position. In the first locking position the first lock element is housed at least partially in a first neck portion of the first tool part such that the first tool part cannot be detached form the first base part. The first base part further comprises a first resilient element pushing the first lock element towards the locking position.

In one embodiment the pusher comprises a washer and the pusher is mounted over the first base element such that the first resilient element pushes the washer against the first lock element for moving the first lock element to the locking position inside the first sloped guide, where the first tool part is engaged.

In one embodiment the pusher is manually operated to move in relation to the first base part pushing the washer against the first resilient element for moving the first lock element to the non-locking position inside the first sloped guide, so that the first tool part can be detached.

In one embodiment the second base part comprises at least one second lock element and a second sloped guide, the second lock element being housed in the second sloped guide and movable from a first locking position to a second non-locking position. In the first locking position the second lock element is housed at least partially in a second neck portion of the second tool part such that the second tool part cannot be detached from the second base part. The second base part further comprises a second resilient element pushing the second lock element towards the locking position.

In one embodiment the cap comprises an inner wall and the cap is mounted over the second base element such that the second resilient element pushes the inner wall against the second lock element for moving the second lock element to the locking position inside the second sloped guide.

In one embodiment the cap is manually operated to move in relation to the second base part pushing the inner wall against the second resilient element for moving the second lock element to the non-locking position inside the second sloped guide so that the second tool part can be detached.

In an alternative embodiment the second base part is movable, actuated by a motor, for pushing the cap against the first base part such that the inner wall pushes against the second resilient element for moving the second lock element to the non-locking position inside the second sloped guide, so that the second tool part can be detached.

In one embodiment the first tool part is a reciprocating cable or a rod and the second part comprises at least a limit switch.

In one embodiment the second base part is joined to a motor or actuator through a force sensor.

BRIEF DESCRIPTION OF THE DRAWINGS

To complete the description and in order to provide for a better understanding of the disclosure, a set of drawings is provided. Said drawings form an integral part of the description and illustrate an embodiment of the disclosure, which should not be interpreted as restricting the scope of the disclosure, but just as an example of how the disclosure can be carried out. The drawings comprise the following figures.

DETAILED DESCRIPTION OF THE DRAWINGS

Figure 1:
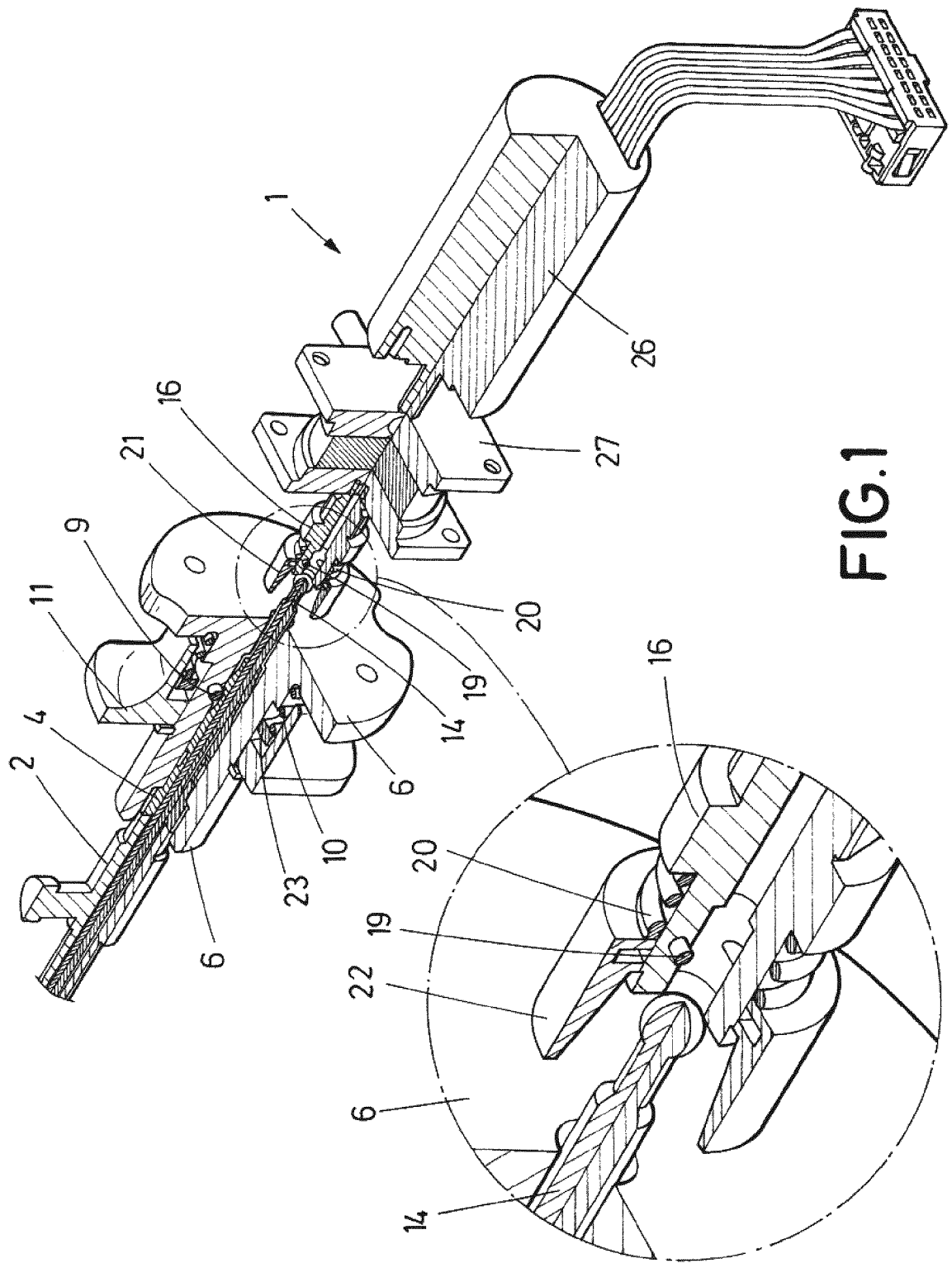
FIG. 1 shows a perspective view of the tool coupling of the disclosure.
Figure 2:
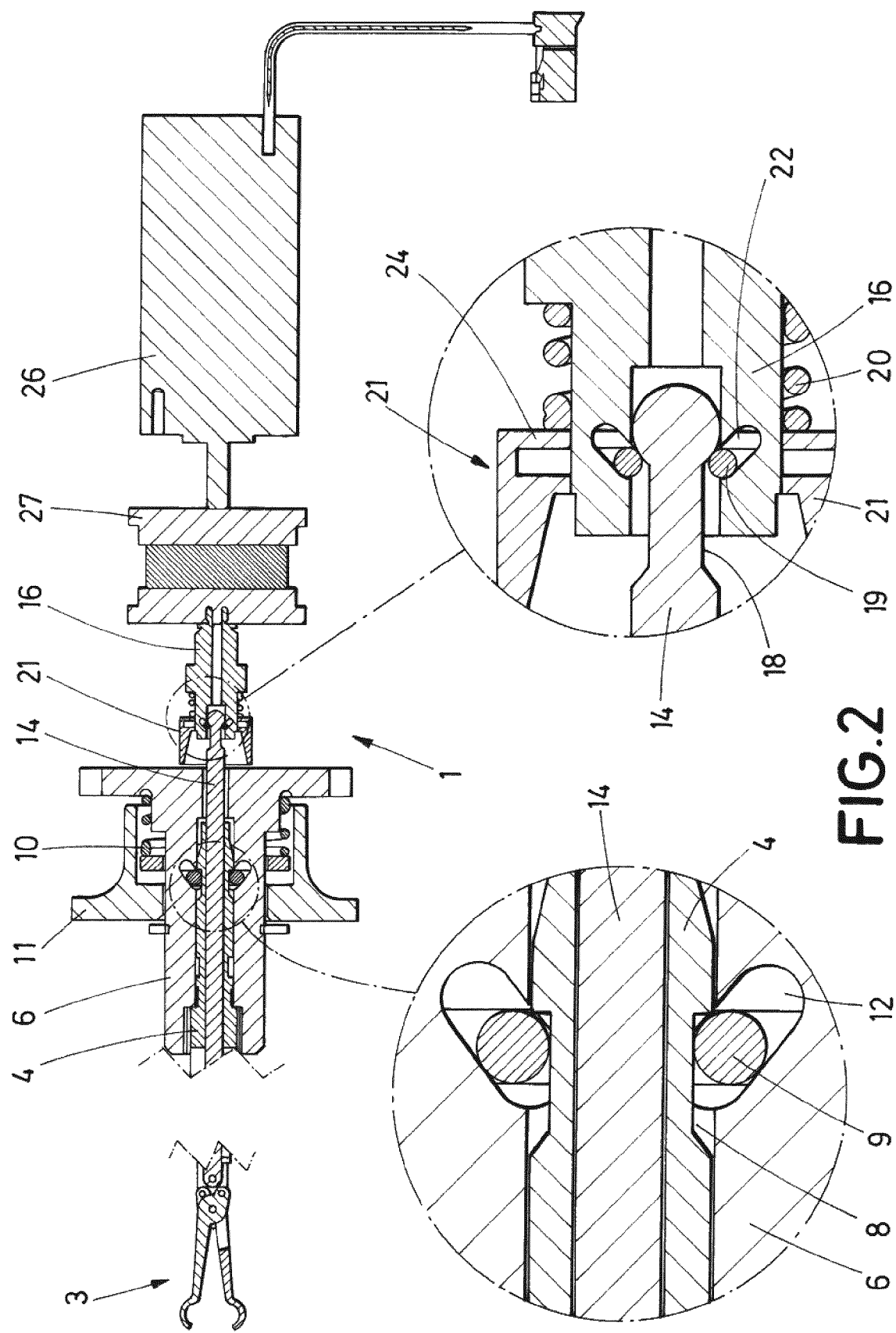
FIG. 2 shows a sectional view of the tool coupling of the disclosure.

FIGS. 1 and 2 illustrate an embodiment of the tool coupling 1 of the disclosure and a tool 2 to be coupled. The tool coupling 1 is placed at the distal end of a machine tool or robot arm.

The tool 2 comprises a first tool part 4 and a second tool part 14. The first tool part 4 is hollow so that the second tool part 14 can move backwards and forward through a channel 5 in the first tool part 4. The tool 2 further comprises a tool head 3 moved by the second tool part 14.

The tool coupling 1 comprises a first base part 6 comprising the components that retain or hold the first tool part 4 and a second base part 16 which can be moved activated by a motor 26 and which can be attached to the second tool part 14 to move the second tool part 14. If the transmitted motion is a reciprocating motion, then the second tool part 14 will move back and forth.

The first base part 6 comprises a first bore 7 corresponding to the first tool part 4, so that the first tool part 4 can be inserted and retained in the first bore 7. The first tool part 4 and the first bore 7 may have corresponding shoulders to limit the insertion of the first tool part 4 in the first bore 7. The first tool part 4 comprises a first neck portion 8 which cooperates with at least one first lock element 9 in the first base part 6. The first lock element 9 is pushed towards the first neck portion 8 by a first resilient element or spring 10, retaining the first tool part 4 inside the first bore 7 of the first base part 6. The first base part 6 comprises a pusher 11 which can be manually pushed to compress the first resilient element 10 such that the first lock element 9 can move outside the first neck portion 8 and thus release the first tool part 4. In the embodiments shown in FIGS. 1 and 2, two such first lock elements 9 are shown. In this embodiment, each first lock element 9 is a rod that traverses the wall of the first bore 7 at each end of the rod in a first sloped guide 12, so that the first lock element 9 can be moved (by the first resilient element 10) to a lock position wherein the first lock element 9 is housed in the first neck portion 8 or can be moved by a washer 13 to an unlocked position inside the first sloped guide 12 so that the first tool part 4 can be detached.

The second tool part 14, as it has already been stated, runs through a channel 5 in the first tool part 4, and is connected to the second base part 16 further from the tool head 3 than the first tool part 4. Similar to said first tool part 4, the second tool part 14 has a second neck portion 18 where at least one second lock element 19 in the second base part 16 engages the second tool part 14. The second lock element 19 is also pushed into the second neck portion 18 by a second resilient element 20, being also in a second sloped guide 22. The second resilient element 20 may be pushed back in order to release the second tool part 14 by moving backwards a cap 21 to compress the second resilient element 20 such that the second lock element 19 can move outside the second neck portion 18. Instead of moving backwards the cap 21, it is possible to move forward the rest of the second base part 16.

Thanks to the first and second sloped guides 12, 22 both the first resilient element 10 and the second resilient element 20 are arranged parallel to the first tool part 4. Therefore, it is possible to place the cap 21 and the pusher 11 facing each other, so that a movement of the second base part 16 towards the first base part 6 will press both the pusher 11 and the cap 21 against the corresponding spring 10, 20, fully freeing the tool 2. The second tool part 14 is connected to a motor 26 or actuator which provides the mechanical power needed to operate the tool head 3. The connection runs through a force sensor 25, which detects in real time the force applied at the tool head 3, and therefore can send the data to a controller (not shown) which reduces or increases said force. In the embodiments shown in FIGS. 1 to 6, motor 26 provides a reciprocating movement along the second tool part 14, but it can also be understood that the power to be transmitted can be torque. In the embodiment shown, one or more limit switches 27 might be installed in the second base part 16 in order to mark the end of the reciprocating movement in one or both directions. Also, this motor 26 or actuator might move the second base part 16 in order to push both the pusher 11 and the cap 21, freeing the first tool part 4.

Both ends of the first tool part 4 and the second tool part 14 are tapered to facilitate the entry in the first bore 7, and temporarily displacing the first 9 and second 19 lock elements. The controller might be a PLC (programmable logic controller) or a human operator who receives feedback though any suitable means (a control screen, lever stiffness, etc.).

Figure 3:
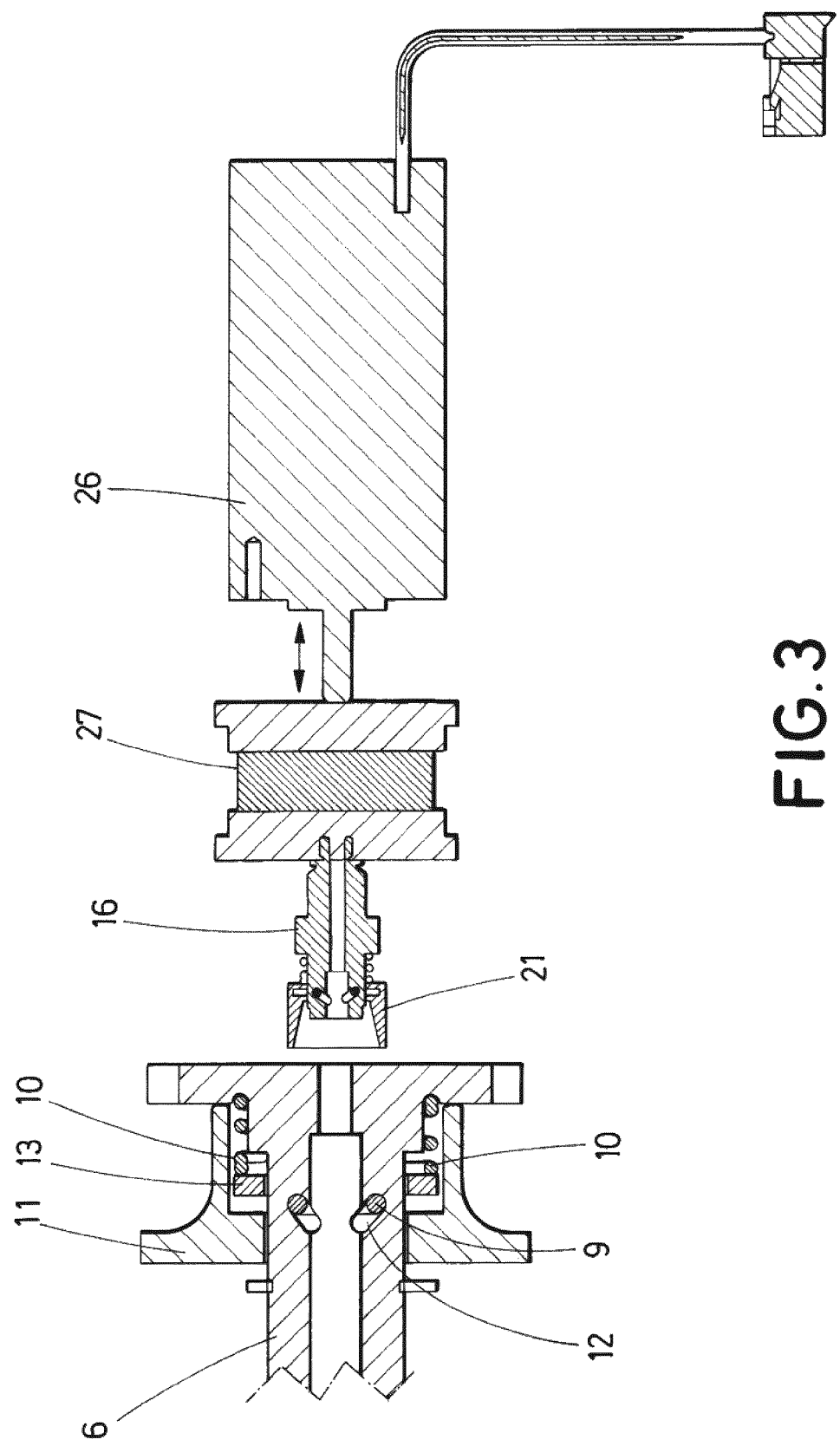
FIG. 3 shows a sectional view of the tool coupling of the disclosure with no tool.
Figure 4:
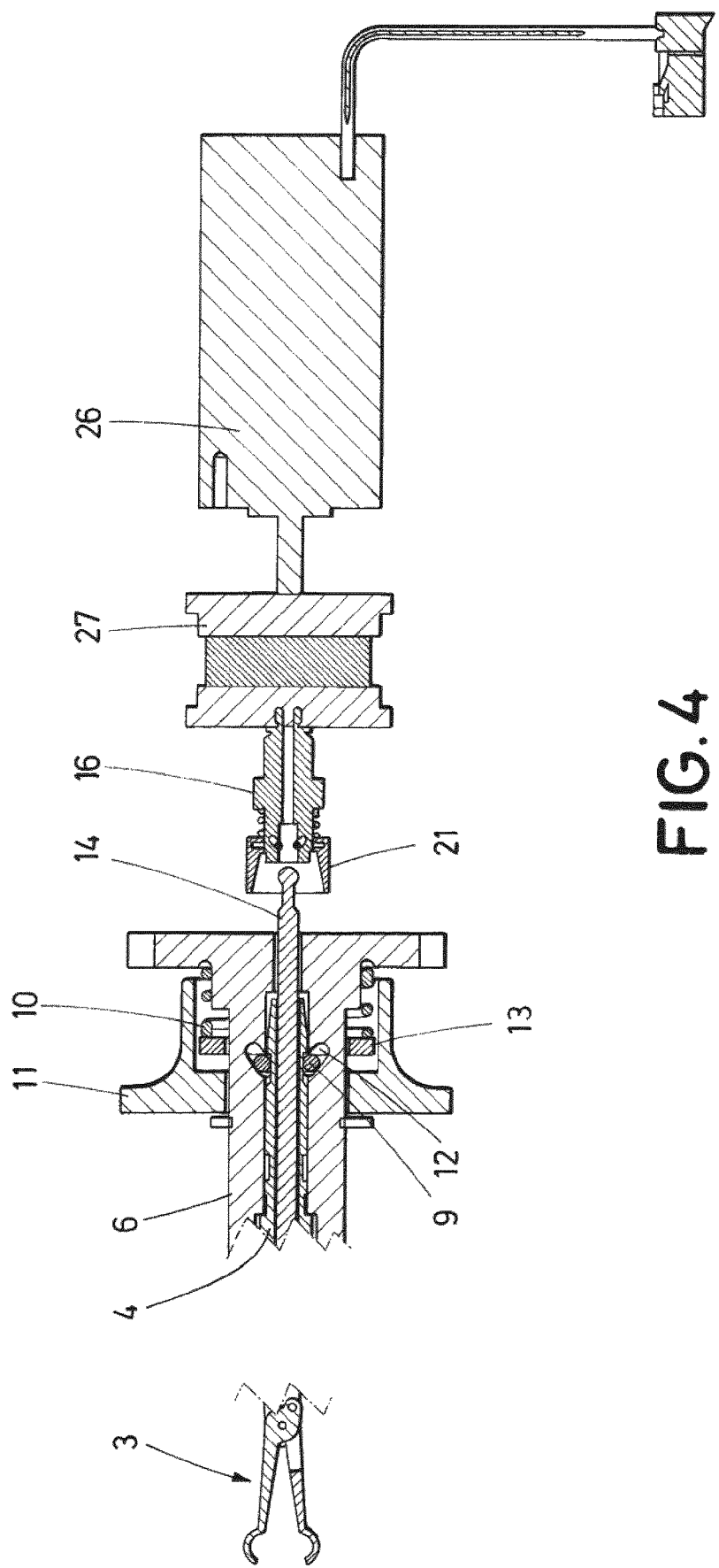
FIG. 4 shows a sectional view of the tool coupling of the disclosure with a first part tool engaged and a second tool part disengaged.

With the tool coupling device of the disclosure the coupling and uncoupling operation are as follows:

FIG. 3 shows the tool coupling 1 with no tool 2 engaged. In that position the pusher 11 contacts the first base part 6. The first lock element 9 being in an unlocked position in the first sloped guide 12. The first lock element 9 is outside the first bore 7 of the first base part 6. Similarly the second lock element 19 is in an unlocked position in the second sloped guide 22. The second lock element 19 is outside the second bore 17 of the second base part 16.

Coupling of the First Tool Part (FIG. 4):

Starting from the position illustrated in FIG. 3, a tool 2 is introduced in the first bore 7 of the first base part 6 pushing the first base part 6, against the force exerted by the first resilient element 10, such that the first base part 6 moves (in the right edge of the first sloped guide 12 in the FIG. 4) and the first lock element 9 moves inside the first sloped guide 22 until it is housed in the first neck portion 8 of the first tool part 4. In this position is not possible to extract the first tool part 4 form the first base part 6 because the first lock element 9 is pressed by the washer 13, pushed by the first lock element 9, so that the first lock element 9 cannot return to the unlocked position, in the left edge of the sloped guide 12 in FIG. 4, The second tool part 14 has not been engaged to the second base part 16.

Coupling of the Second Tool Part (FIG. 5):

The second tool part 14 pushes the second base part 16, against the force of the second resilient element 20 and the second lock element 19 moves inside the second sloped guide 22 until it is housed in the second neck portion 18 of the second tool part 14. In this position is not possible to extract the second tool part 14 form the second base part 16 because the second lock element 19 is pressed by the inner wall 24 of the cap 21, pushed by the second lock element 19, so that the second lock element 19 cannot return to the unlocked position (in the right edge of the sloped guide 22 in FIG. 5).

Figure 5:
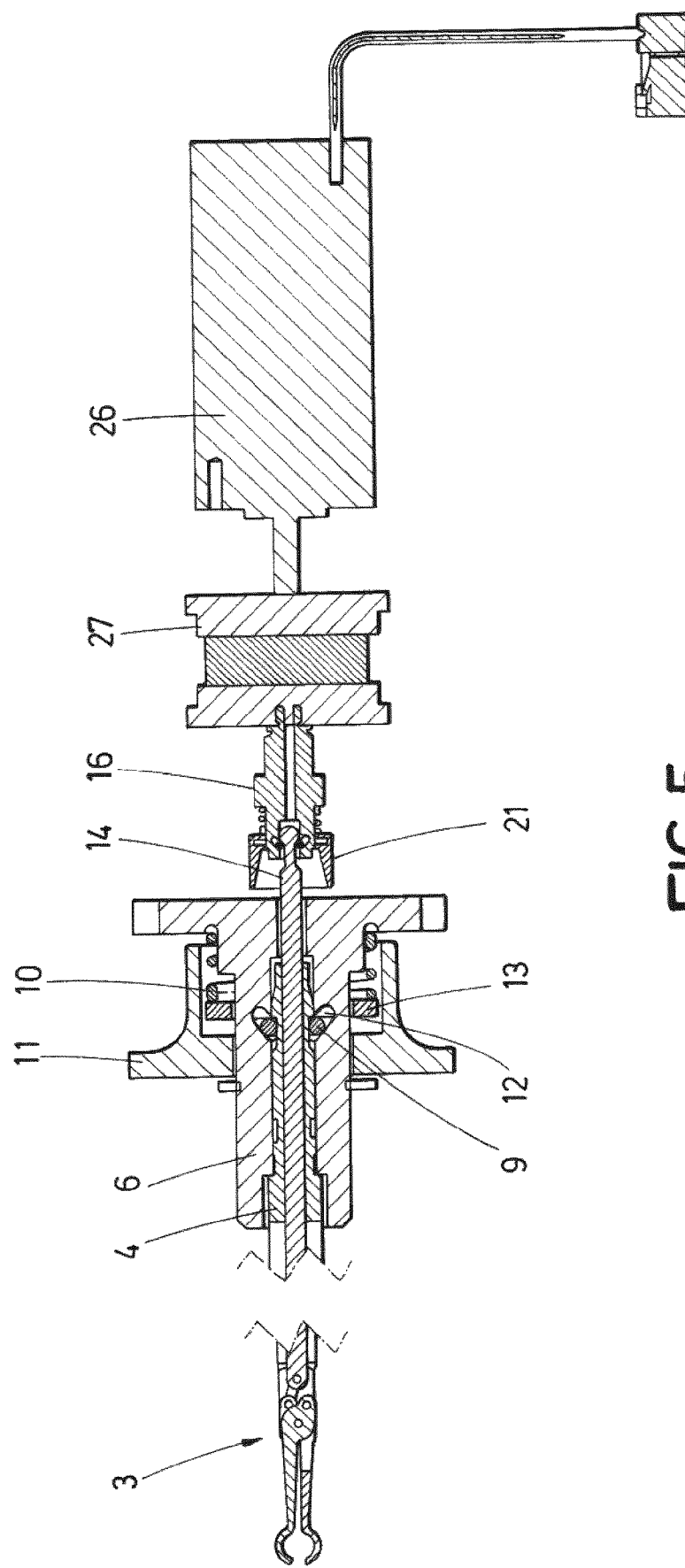
FIG. 5 shows a sectional view of the tool coupling of the disclosure with a first part tool engaged and a second tool part engaged.

In FIG. 5 both the first and the second tool part are engaged and the tool is completely engaged.

Figure 6:
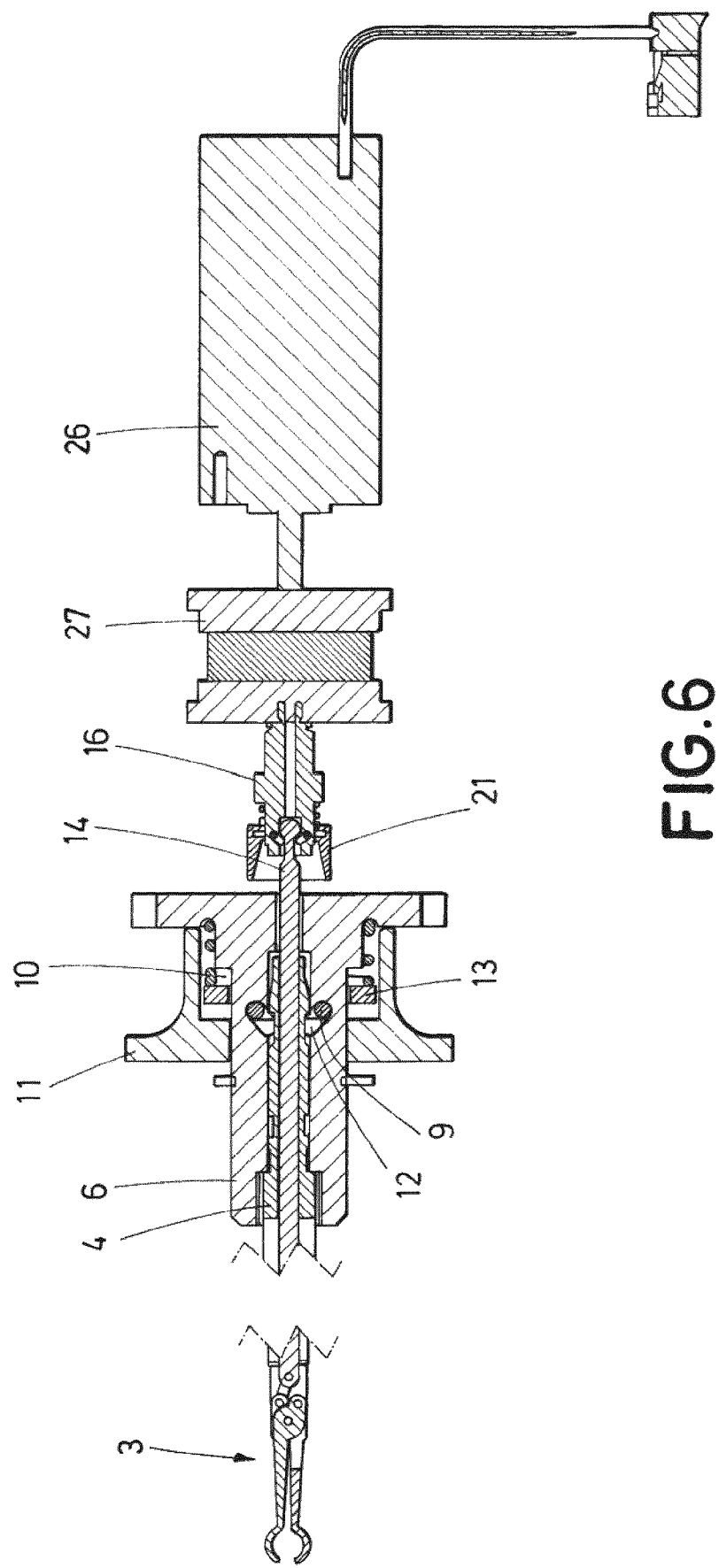
FIG. 6 shows a sectional view of the tool coupling of the disclosure with a first part tool and a second tool part unlocked and enabled to be disengaged.

Uncoupling of the Second Tool Part (FIG. 6):

Pushing the cap 21 against the force of the second resilient element 20 (to the right in FIG. 6) the inner wall 24 of the cap 21 pushes the second lock element 19 to the unlocked position (in the right edge of the second sloped guide 22 in FIG. 6).

Uncoupling of the First Tool Part (FIG. 6):

Pushing the pusher 11 against the force of the first resilient element 10, to the left in FIG. 6, the washer 13 of the pusher 11 pushes the first lock element 9 to the unlocked position, in the left edge of the first sloped guide 12 in FIG. 6.

Figure 7:
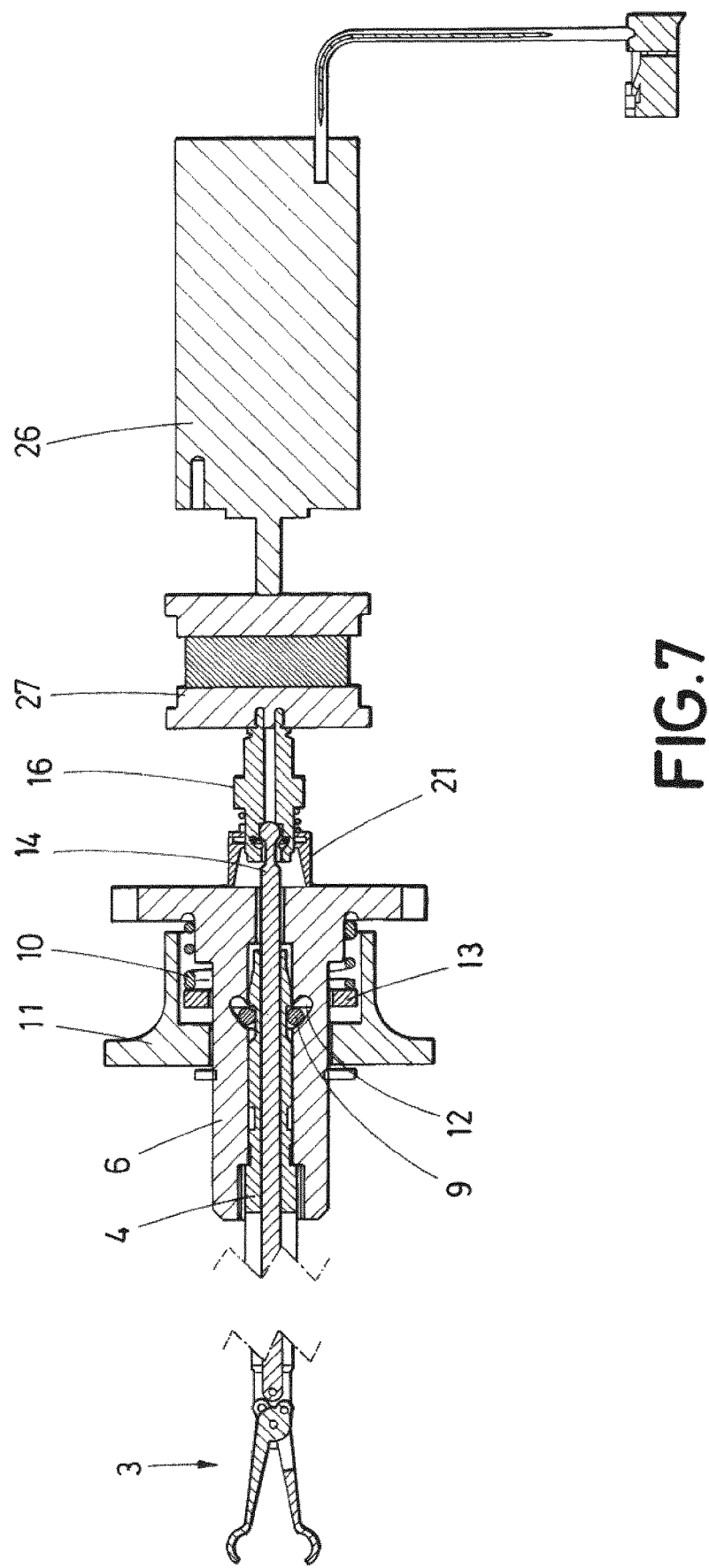
FIG. 7 shows a sectional view of the tool coupling of the disclosure with a first part tool engaged and a second tool part unlocked and enabled to be disengaged.

FIG. 7 illustrates a different way for de uncoupling of the tool 2. In this embodiment the activation motor 26 moves the second base part 16 (to the left in FIG. 7) pushing the cap 21 against the first base part 6 until the cap 21 moves backwards (to the right in FIG. 7) in relation to the movement of the second base part 16. The cap 21 compresses the second resilient element 20 such that the second lock element 19 moves inside the second sloped guide 22 to the unlocked position, unlocking the second tool part 14. A further activation of the motor 26 provokes a further movement of the second base part 16 pushing the first base part 6 (to the left in FIG. 7) compressing the first resilient element 10 such that the first lock element 9 moves inside the first sloped guide 12 to the unlocked position, unlocking the first tool part 4.

In this text, the term "comprises" and its derivations (such as "comprising", etc.) should not be understood in an excluding sense, that is, these terms should not be interpreted as excluding the possibility that what is described and defined may include further elements, steps, etc.

The disclosure is obviously not limited to the specific embodiment(s) described herein, but also encompasses any variations that may be considered by any person skilled in the art (for example, as regards the choice of materials, dimensions, components, configuration, etc.), within the general scope of the disclosure as defined in the claims.

The invention claimed is:

1. A tool coupling for coupling to a base a tool comprising a first tool part and a second tool part, the second tool part being movable in relation to the first tool part wherein the tool coupling comprises a first base part for detachably retaining the first tool part of the tool to be coupled and a second base part movable in relation to the first base part for detachably retaining the second tool part of the tool to be coupled, wherein:
   the first base part comprises a pusher movable in relation to the first base part for, when a tool is coupled to the tool coupling, detaching the first tool part, and
   the second base part comprises a cap movable in relation to the second base part for, when a tool is coupled to the tool coupling, detaching the second tool part,
   the second base part being movable, with a reciprocating motion, activated by a motor and attachable to the second tool part of the tool to be coupled to move the second tool part back and forth, where the second base part is joined to a motor or actuator through a force sensor,
   wherein the first base part comprises at least one first lock element and a first sloped guide, the first lock element being housed inside the first sloped guide and movable from a locking position to a non-locking position, wherein in the locking position, the first lock element is housed at least partially in a first neck portion of the first tool part such that the first tool part cannot be detached form the first base part, the first base part further comprising a first resilient element for pushing the first lock element towards the locking position,
   wherein a pusher comprises a washer and the pusher is mounted over the first base part such that the first resilient element pushes the washer against the first lock element for moving the first lock element to the locking position inside the first sloped guide, so that the first tool part is engaged.

2. The tool coupling according to claim 1, wherein the pusher is manually operated to move in relation to the first base part pushing the washer against the first resilient element for moving the first lock element to the non-locking position inside the first sloped guide so that the first tool part can be detached.

3. The tool coupling, according to claim 1, wherein the second base part comprises at least one second lock element and a second sloped guide, the second lock element being housed in the second the sloped guide and movable from a locking position to a non-locking position, wherein in the locking position the second lock element is housed at least partially in a second neck portion of the second tool part such that the second tool part cannot be detached form the second base part, the second base part further comprising a second resilient element pushing the second lock element towards the locking position.

4. The tool coupling according to claim 3, wherein the cap comprises an inner wall and the cap is mounted over the second base part such that the second resilient element pushes the inner wall against the second lock element for moving the second lock element to the locking position inside the second sloped guide so that the second tool part is engaged.

5. The tool coupling according to claim 4, wherein the cap is manually operated to move in relation to the second base part pushing the inner wall against the second resilient element for moving the second lock element to the non-locking position inside the second sloped guide so that the second tool part can be detached.

6. The tool coupling according to claim 3, wherein the second base part is movable, actuated by a motor, for pushing the cap against the first base part such that the inner wall pushes against the second resilient element for moving the second lock element to the non-locking position inside the second sloped guide so that the second tool part can be detached.

7. The tool coupling, according to claim 1, wherein the second tool part is a reciprocating cable or a rod.

8. The tool coupling, according to claim 1, wherein the base is a robot arm or a machine-tool.

* * * * *